United States Patent
Anderson et al.

(10) Patent No.: US 6,369,248 B1
(45) Date of Patent: Apr. 9, 2002

(54) FRAGRANCE PRECURSOR COMPOUNDS

(75) Inventors: Denise Anderson, Zürich; Georg Frater, Winterthur, both of (CH)

(73) Assignee: Givaudan SA (CH)

( * ) Notice: Subject to any disclaimer, the term of this patent is extended or adjusted under 35 U.S.C. 154(b) by 0 days.

(21) Appl. No.: 09/446,257

(22) PCT Filed: Jun. 22, 1998

(86) PCT No.: PCT/EP98/03772

§ 371 Date: Dec. 20, 1999

§ 102(e) Date: Dec. 20, 1999

(87) PCT Pub. No.: WO98/58899

PCT Pub. Date: Dec. 30, 1998

(30) Foreign Application Priority Data

Jun. 21, 1997 (EP) ............................................. 97110195

(51) Int. Cl.$^7$ ........................ C07C 233/05; A61K 7/32
(52) U.S. Cl. ........................ 554/61; 252/8.63; 424/65; 514/532; 514/617; 554/35; 554/213; 560/60; 564/170
(58) Field of Search ........................ 564/170; 560/60; 514/617, 532; 424/65; 554/35, 61, 213; 252/8.63

(56) References Cited

U.S. PATENT DOCUMENTS 4,473,085 A * 9/1984 Grubbs et al. ................ 560/60
5,726,345 A    3/1998 Paget et al.

FOREIGN PATENT DOCUMENTS

WO    WO 95/04809    of 1995

OTHER PUBLICATIONS

Heymann, H., et al., *J. Amer. Chem. Soc.*, 67, p. 1979, (1945).
Brown, H.C., et al., *J. Org. Chem.*, 485–487, (1966).
*Comprehensive Organic Chemistry*, Derek Barton & W. David Ollis, eds., 2, 871–907, (1979).
Huffer, M., et al., *Tetrahedron: Asymmetry*, 2(11):1157–1164, (1991).
Rosenmund, K.W., et al., *Arch. Pharm. Ber. Dtsch Pharm. Ges.*, 293, 245–251, (1960).
Beilstein Database Registry No. 2361081 (XP–002082020), 1960.
Beilstein Database Registry No. 3603443 (XP–002082019), 1990.
Patent Abtract of Japan, publication No. JP 08182498 (1996) (European Patent Office).
Jacobs, H., et al., *Synthetic Communications*, 20(7):999–1010 (1990).
Kabara, J.J., *Cosmet. Sci. Technol. Ser.*, 16, 181–208 (1997).
Ruholl, H., et al., Synthesis, 408–409, (1987).
Hassner, A., et al. *Tetrahedron Letters*, 46, 4475–4478, (1978).
Robertson et al, J. Org. Chem., vol. 48, No. 26, pp. 5288–5302, 1983.*

* cited by examiner

*Primary Examiner*—Shailendra Kumar

(57) ABSTRACT

Compounds having formula (I) in which n is 1, 2 or 3 and $R^1$ to $R^6$ represent, independently, branched or unbranched, substituted or unsubstituted alkyl-, alkenyl-, alkinyl-, cycloalkyl-, cycloalkenyl- or aromatic-radicals or hydrogen wherein these radicals may in addition contain one or more —O— and/or (a)—groups, whereby one or two rings can be built by the combination of the respective $R^1$ to $R^6$ and this/these ring(s) can be further substituted by an alkyl-group, in which X is either O and $R^7$ represents a radical of an alcohol or phenol $R^7OH$, or X is N and $R^7$ represents the radical of an amine $R^7R^{7''}NH$, whereby $R^{7'}$ and $R^{7''}$ represent independently, branched or unbranched, substituted or unsubstituted alkyl-, alkenyl-, alkinyl-, cycloalkyl-, cycloalkenyl- or aromatic radicals or either $R^{7'}R^{7''}$ may be hydrogen, whereby the amine is a fragrant amine or the amine has more than 9 C atoms, whereby $R^{7'}$ of the alcohol or phenol and $R^{7'}$ and/or $R^{7''}$ of the amine, respectively, may further contain at least one remaining part $C(OH)R^1R^2$—$CR^3R^4$—$(CR^5R^6)_n$—CO— of formula (I), are useful as precursors for the delivery of odoriferous and/or antibacterial compounds in cosmetic compositions, cosmetic products, air fresheners, hard surface cleaners or laundry products.

(I)

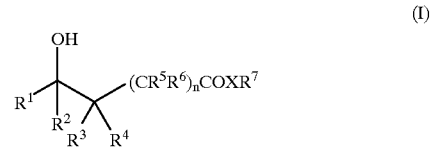

30 Claims, No Drawings

FRAGRANCE PRECURSOR COMPOUNDS

This application is a 371 of PCT/EP98/03772, filed Jun. 22, 1998.

The invention relates to fragrance and/or antibacterial precursor compounds. In particular, the invention relates to the use of compounds which can act as fragrance and/or antibacterial precursors in cosmetic products such as deodorants and antiperspirants and in laundry products such as detergents and fabric softeners or in air fresheners or hard surface cleaners. These compounds are normally odourless or nearly so, but upon contacting the skin as for example, in skin care compositions or in personal care compositions, produce fragrances. The compounds also produce fragrances when used in the presence of enzymes such as lipases and proteases, e.g. used in (laundry) detergents and fabric softeners, thus providing a prolongation of the fabric scenting effect. The compounds can also produce fragrances when heated.

A principal strategy currently employed in imparting odours to consumer products is the admixing of the fragrance directly into the product. There are however, several drawbacks to this strategy. The fragrance material can be too volatile, resulting in fragrance loss during manufacturing, storage, and use. Many fragrance materials are also unstable over time. This again results in loss during storage.

In some cases, fragrances are microencapsulated or treated with cyclodextrins to form inclusion complexes to help decrease volatility and improve stability. However, these methods are for a number of reasons often not successful. In addition, cyclodextrins can be too expensive.

In many consumer products it is desirable for the fragrance to be released slowly over time. Microencapsulation and cyclodextrins have been used to provide slow-release properties, however, they are subject to the same limitations as above.

The present invention now provides compounds which show a low level of odour, or are even odourless, and can be cleaved under activating conditions, e.g. by heat or by an acid, a base, bacteria or enzymes, to give fragrant molecules. So, for example, the compounds of the invention are odourless prior to application to the skin, but release fragrant molecules after application to the skin, that is, they provide a delayed release of the fragrance, in particular to the skin in the axilla which is the result of the cleavage by bacteria. The compounds of the present invention also release fragrant molecules when used in the presence of enzyme-containing products and, this way, provide a prolongation of the fabric scenting effect. The compounds of the present invention also release fragrant molecules when heated.

The compounds under consideration are compounds of the formula

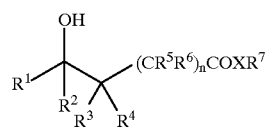

I in which n is 1, 2 or 3 and $R^1$ to $R^6$ represent, independently, branched or unbranched, substituted or unsubstituted alkyl-, alkenyl-, alkinyl-, cycloalkyl-, cycloalkenyl- or aromatic-radicals or hydrogen wherein these radicals may in addition contain one or more —O— and/or

groups, whereby one or two rings can be build by the combination of the respective $R^1$ to $R^6$ and this/these ring(s) can be further substituted by an alkyl-group, in which X is either O and $R^7$ represents a radical of an alcohol or phenol $R^7OH$ or X is N and $R^7$ represents the radical of an amine $R^{7'}R^{7''}NH$, whereby $R^{7'}$ and $R^{7''}$ represent independently, branched or unbranched, substituted or unsubstituted alkyl-, alkenyl-, alkinyl-, cycloalkyl-, cycloalkenyl- or aromatic radicals or either $R^{7'}$ $R^{7''}$ may be hydrogen, whereby the amine is a fragrant amine or the amine has more than 9 C atoms, whereby $R^7$ of the alcohol or phenol and $R^{7'}$ and/or $R^{7''}$ of the amine, respectively, may further contain at least one remaining part $C(OH)R^1R^2$—$CR^3R^4$—$(CR^5R^6)_n$—CO— of formula I. Thus, the precursor compounds are esters of formula Ia

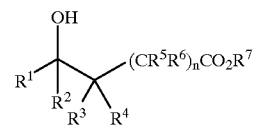

Ia in which n is 1, 2 or 3 and $R^1$ to $R^6$ represent, independently, branched or unbranched, substituted or unsubstituted alkyl-, alkenyl-, alkinyl-, cycloalkyl-, cycloalkenyl- or aromatic-radicals or hydrogen wherein these radicals may in addition contain one or more —O— and /or

groups, $R^7$ represents a radical of an alcohol or phenol $R^7OH$, whereby one or two rings can be build by the combination of the respective $R^1$ to $R^6$ and this/these ring(s) can be further substituted by an alkyl-group, whereby $R^7$ may further contain the remaining part $C(OH)R^1R^2$—$CR^3R^4$—$(CR^5R^6)_n$—CO— of formula Ia, or amides of formula Ib

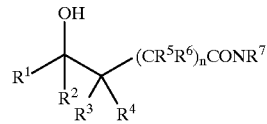

Ib in which n is 1, 2 or 3 and $R^1$ to $R^6$ represent, independently, branched or unbranched, substituted or unsubstituted alkyl-, alkenyl-, alkinyl-, cycloalkyl-, cycloalkenyl- or aromatic-radicals or hydrogen wherein these radicals may in addition contain one or more —O— and /or

groups, whereby one or two rings can be build by the combination of the respective $R^1$ to $R^6$ and this/these ring(s) can be further substituted by an alkyl-group, and $R^7$ represents a radical of an amine R⁷'R⁷"NH, whereby R⁷' and R⁷" represent, independently, branched or unbranched, substituted or unsubstituted alkyl-, alkenyl-, alkinyl-, cycloalkyl-, cycloalkenyl- or aromatic radicals or either R⁷' or R⁷" may be hydrogen, whereby the amine is a fragrant amine or the amine has more than 9 C atoms, whereby R⁷' and/or R⁷" may further contain at least one remaining part C(OH)R¹R²—CR³R⁴—(CR⁵R⁶)ₙ—CO— of formula Ib. With respect to the precursor compounds of formula Ia specifically the invention is related to those compounds in which n is 1, 2 or 3 and R¹ to R⁶ represent, independently, substituted or unsubstituted alkyl-, alkenyl-, alkinyl-, cycloalkyl-, cycloalkenyl- or aromatic-radicals or hydrogen wherein these radicals may in addition contain one or more —O— and/or

groups, R⁷ represents a radical of a fragrant alcohol R⁷OH, whereby one or two rings can be build by the combination of the respective R¹ to R⁶ and this/these ring(s) can be further substituted by an alkyl-group.

Further characteristics and advantages of the invention are described by claims 4 to 29 and by the following description and examples.

The compounds of formula I are not limited to any particular stereoisomers, all possible stereoisomers (enantiomers, diastereomers) and all mixtures are thus included within the scope of formula I.

The compounds of formula I may preferably be used as sustained release odorants but also to mask or attenuate undesirable odours or to provide additional odours not initially present in consumer products, i.e. laundry detergents, fabric softeners, fabric softeners sheets, hard surface cleaners, automatic dishwasher detergents and (other) enzyme-containing consumer products. Additional applications include cosmetic products destined for application to human skin such as underarm deodorants or antiperspirants or other deodorants contacting the body, or in hand lotions, baby powders, baby lotions, ointments, foot products, facial cleansers, body wipes, facial make-up, colognes, after-shave lotions, shaving creams, etc. Further additional applications include ironing treatments and air fresheners dispensed via heat.

The compounds of formula I may be used individually in an amount effective to enhance the characteristic odour of a material. More commonly, however, the compounds are mixed with other fragrance components in an amount sufficient to provide the desired odour characteristics.

The amount required to produce the desired, overall effect varies depending upon the particular compounds of formula I chosen, the product in which it will be used, and the particular effect desired.

For example, depending upon the selection and concentration of the compound(s) of formula I chosen, when added either singly or as a mixture, e.g. to a deodorant, laundry product, hard surface cleaner or air freshener composition at levels ranging from about 0.1 to about 10% by weight, or most preferred about 0.25 to about 4% by weight, an odorant, i.e. an odoriferous alcohol and an odoriferous lactone in an organoleptically effective amount is released when the product is used. These newly formed odorants serve to enhance the odour of the fragrance.

The compounds of formula I can accordingly be used in the manufacture of odorant compositions used in the preparation of air fresheners, cosmetic and laundry products e.g. deodorants, antiperspirants, laundry detergents, fabric softeners, hard surface cleaners, and as is evident from the above compilation, a broad range of known odorants or odorant mixtures can be used. In the manufacture of such compositions the known odorants or odorant mixtures set forth above can be used according to methods known to a person skilled in the art, normally a perfumer, or described e.g. in W. A. Poucher, Perfumes, Cosmetics, Soaps, 2, 7th Edition, Chapman and Hall, London 1974.

Concerning the esters suitable examples of odoriferous alcohols R⁷OH are alcohols or phenols such as listed in Table 1.

Table 1 amyl alcohol
hexyl alcohol*
hexyl alcohol*
heptyl alcohol*
octyl alcohol*
nonyl alcohol*
decyl alcohol*
undecyl alcohol*
lauryl alcohol*
myristic alcohol
3-methyl-but-2-en-1-ol*
3-methyl-1-pentanol
cis-3-hexenol**
cis-4-hexenol*
3,5,5-trimethyl hexanol
3,4,5,6,6-pentamethylheptan-2-ol*
citronellol**
geraniol**
oct-1-en-3-ol
2,5,7-trimethyl octan-3-ol
2-cis-3,7-dimethyl-2,6-octadien-1-ol
6-ethyl-3-methyl-5-octen-1-ol*
3,7-dimethyl-oct-3,6-dienol*
3,7-dimethyloctanol**
7-methoxy-3,7-dimethyl-octan-2-ol*
cis-6-nonenol*
5-ethyl-2-nonanol
6,8-dimethyl-2-nonanol*
2,2,8-trimethyl-7 (8)-nonene-3-ol
nona-2,6-dien-1-ol
4-methyl-3-decen-5-ol**
dec-9-en-1-ol
benzylalcohol
2-methyl undecanol
10-undecen-1-ol
1-phenyl ethanol*
2-phenyl ethanol**
2-methyl-3-phenyl-3-propenol
2-phenyl propanol*
3-phenyl propanol*
4-phenyl-2-butanol
2-methyl-5-phenyl pentanol*
2-methyl-4-phenyl-pentanol*
3-methyl-5-phenyl-pentanol*
2-(2-methylphenyl)-ethanol*
4-(1-methylethyl)benzene methanol
4-(4-hydroxyphenyl)butan-2-one*
2-phenoxy ethanol*
4-(1-methylethyl)-2-hydroxy-1-methyl benzene
2-methoxy-4-methyl phenol
4-methyl phenol
anisic alcohol* p-tolyl alcohol*
cinnamic alcohol**
vanillin*
ethyl vanillin*
eugenol**
isoeugenol**
thymol
anethol*
decahydro 2-naphthalenol
borneol*
cedrenol*
farnesol*
fenchyl alcohol*
menthol* 3,7,11-trimethyl-2,6,10-dodecatrien-1-ol alpha ionol* tetrahydro ionol*
2-(1,1-dimethylethyl)cyclohexanol*
3-(1,1-dimethylethyl)cyclohexanol*
4-(1,1-dimethylethyl)cyclohexanol*
4-isopropyl cyclohexanol
6,6-dimethyl-bicyclo [3.3.1]hept-2-ene-2-ethanol
6,6-dimethyl-bicyclo [3.1.1]hept-2-ene-methanol*
p-menth-8-en-3-ol*
3,3,5-trimethyl cyclohexanol
2,4,6-trimethyl-3-cyclohexenyl-methanol*
4-(1-methylethyl)cyclohexyl-methanol*
4-(1,1-dimethylethyl)cyclohexanol
2-(1,1-dimethylethyl)-cyclohexanol
2,2,6-trimethyl-alpha-propyl cyclohexane propanol*
5-(2,2,3-trimethyl-3-cyclopentenyl)-3-methylpentan-2-ol*
3-methyl-5-(2,2,3-trimethylcyclopentyl-3-enyl)pent-4-en-2-ol**
2-ethyl-4(2,2,3-trimethylcyclopentyl-3-enyl)but-2-en-1-ol**
4-(5,5,6-trimethylbicyclo[2.2.1]hept-2-yl)-cyclohexanol*
2-(2-methylpropyl)-4-hydroxy-4-methyl-tetrahydropyran*
2-cyclohexyl propanol*
2-(1,1-dimethylethyl)-4-methyl cyclohexanol*
1-(2-tert-butyl-cyclohexyloxy)-2-butanol*
1-(4-isopropyl-cyclohexyl)-ethanol*
linalool **
2,6-dimethyl-heptan-2-ol**
2,6-dimethyl-oct-7-en-2-ol**
whereby one asterisk indicates the preferred alcohols and phenols and two asterisks indicate the more preferred alcohols and phenols.

It is a matter of course, that it is not possible to give a complete list of the odoriferous alcohols and phenols R$^7$OH which are liberated as a result of the desired cleavage of the compounds of formula I as mentioned above, especially by heat, enzymes or by bacteria, and which alcohols are then capable of imparting agreeable odours. The skilled artisan is, however, quite aware of those alcohols and phenols, which provide a positive contribution to the fragrance compositions.

But the alcohol or phenol constituting the radical R$^7$ can also be a non-odoriferous one or a polyalcohol. Thus, the radical R$^7$ can be derived from as well a simple alcohol like e.g. methanol or ethanol as also from a fatty alcohol or a compound such as 7-hydroxy-4-methyl coumarin.

Examples of polyalcohols constituting the radical R$^7$ in the compounds of formula I, or more specifically of formula Ia, are:
diols such as: diethylene glycol, propylene glycol, triethylene glycol, N-butyldiethanol amine, 1,3-bis-(4-hydroxy butyl)-1,1,3,3 tetramethyl-disiloxane, 4,4'-bicyclohexyldiol;
triols such as: glycerol, 1,3,5-cyclohexantriol;
sugars such as: furanoside and pyranoside sugars such as glucose, fructose;
polymers such as: hydroxyethylcellulose, hydroxypropyl-cellulose.

Compounds of formula I upon cleavage may also generate antimicrobial compounds. Examples of these compounds are e.g. presented by J. J. Kabara, Cosmet. Sci. Technol. Ser. (16) 1997, p 181–208, especially in Table 8.6.

Of course, the afore mentioned alcohols, phenols and antimicrobial compounds can serve mutually as fragrances and antimicrobial compounds, respectively. A person of skill in the art is well aware of these interrelationships and can make use thereof to solve a specific problem by using the precursors of the present invention.

The compounds of formula Ia are virtually odourless under room temperature and atmospheric conditions, i.e. about 10 to about 40 degrees Celsius and about 20 to 100% relative humidity. However, when applied to the body or when used in an application in the presence of enzymes such as lipases and proteases, or when heated they undergo a transformation in which the alcohol or phenol and lactone are released.

The compounds of formula Ia, upon cleavage, provide alcohols or phenols and lactones having organoleptic properties and therefore permit the development of methods useful in enhancing the odour of consumer products.

Suitable examples of such lactones are listed in Table 2.

Table 2

6-methyl-pyran-2-one
5-heptyldihydro-2(3H)-furanone*
5-pentyldihydro-2(3H)-furanone*
5-(3-hexenyl)dihydro-5-methyl-(Z)-2(3H)-furanone
5-hexyldihydro-5-methyl-2(3H)-furanone
5-hexyldihydro-2(3H)-furanone*
5-octyldihydro-2(3H)-furanone
8-(1-methylethyl)-1-oxaspiro[4.5]-decan-2-one*
8-methyl-1-oxaspiro[4.5]-decan-2-one
8-ethyl-1-oxaspiro[4.5]-decan-2-one
5-(1,5-dimethyl-4-hexenyl)dihydro-2(3H)-furanone
2-oxo-5-butyl-tetrahydrofuran*
4-methyl-5-pentyl-dihydro-2(3H)-furan-2-one
5-hexyldihydro-5-methyl-2(3H)-furanone
dihydro-5-methyl-5-vinyl-2(3H)-furanone
octahydro-2H-1-benzopyran-2-one
tetrahydro-6-pentyl-2H-pyran-2-one
tetrahydro-6-hexyl-2H-pyran-2-one
tetrahydro-6-heptyl-2H-pyran-2-one
tetrahydro-6-(3-pentenyl)-(E)-2H-pyran-2-one
tetrahydro-6-(2-pentenyl)-(Z)-2H-pyran-2-one
whereby the asterisks indicate the preferred lactones. Table 2 is not complete but shows only representative lactones with positive effect in connection with the present invention. A person skilled in the art is, however, quite aware to further lactones which provide a positive contribution to the enhancement of the odour of consumer products.

The compounds of formula Ia can be prepared by using standard methods known to a person skilled in the art. For example, they can be prepared in two steps from keto acids. Esters of the keto acids may be prepared by standard methods known to those skilled in the art, see Comprehensive Organic Chemistry, Derek Barton and W. David Ollis, eds., Vol. 2, 1979, pp.871–907. For example, esters are formed by the acid catalyzed reaction between a carboxylic acid and an alcohol. During the condensation water is usually removed.

Either protic or Lewis acids may be used. Some acids which may be used are p-toluenesulfonic acid, sulfuric acid, and pyridinium p-toluenesulfonate. A variety of inert solvents may be used such as toluene, xylene, cyclohexane, and hexane.

In another method which may be used for the preparation of the compounds of formula Ia, an appropriate carboxylic acid and an appropriate alcohol react to form an ester when treated with N,N'-dicyclohexylcarbodiimide and 4-pyrrolidinopyridine, see e.g. the procedure of Hassner and Alexanian, Tetrahedron Letters 4475, (1978).

These esters can then be reduced to the compounds of formula I by using standard methods known to a person skilled in the art. Reagents for the transformation include sodium borohydride and lithium aluminum hydride.

Compounds of formula Ia can also be prepared directly from the corresponding alcohol and lactone, see e.g. J. Org. Chem. (1966), 485.

The most preferred precursor compounds according to the invention are esters of one alcohol out of the group citronellol, phenylethyl alcohol, geraniol and cis-3-hexanol, specifically compounds selected from the group consisting of 4-hydroxy-decanoic acid 2-phenethyl ester, 4-hydroxy-decanoic acid 3,7-dimethyl-oct-6-enyl ester, 4-hydroxy-decanoic acid hex-3-enyl ester, 4-hydroxy-decanoic acid 3,7-dimethyl-oct-2,6-dienyl ester, 5-hydroxy-dodecanoic acid 3,7-dimethyl-oct-6-enyl ester, 5-hydroxy-dodecanoic acid 3,7-dimethyl-oct-2,6-dienyl ester, 4-hydroxy-undecanoic acid 3,7-dimethyl-oct-6-enyl ester, 4-hydroxy undecanoic acid 3,7-dimethyl-oct-2,6 dienyl ester, 4-hydroxy-decanoic acid 1,5-dimethyl-1-vinyl-hex-4-enyl ester, 4-hydroxy-decanoic acid 1,1,5-trimethyl-hept-6-enyl ester, 4-hydroxy-decanoic acid 1,1,5-trimethyl-hexyl ester, 4-hydroxy-undecanoic acid 3,7-dimethyl-oct-6-enyl ester, 4-hydroxy-undecanoic acid phenethyl ester, 4-hydroxy-undecanoic acid hex-3-enyl ester, 4-hydroxy-nonanoic acid 3,7-dimethyl-octa-2,6-dienyl ester, 4-hydroxy-nonanoic acid 3,7-dimethyl-oct-6-enyl ester, 4-hydroxy-nonanoic acid hex-3-enyl ester, 4-hydroxy-nonanoic acid phenethyl ester, 3-(1-hydroxy-4-isopropyl-cyclohexyl)-propionic acid 3,7-dimethyl-octa-2,6-dienyl ester and 4-hydroxy-undecanoic acid 2-(4-hydroxy-undecanoyloxy)-ethyl ester.

Concerning the second group of the precursor compounds according to the invention under activating conditions, the hydroxy amide will cleave to release a lactone and an amine. The lactone may have organoleptic properties.

There are basically three classes of amine products to build the amides according to the invention:
  non-odoriferous amines which can be primary or secondary amines and have more than nine carbon atoms. Preferable amines are those with an affinity to fiber and those used in cosmetic and laundry formulations,
  odoriferous amines,
  non-odoriferous amines substituted with an odoriferous group. For example, the amine may be substituted by a group such as —$CO_2R$, —$OCO_2R$ wherein R represents a radical of a fragrant alcohol or the enol form of a fragrant aldehyde or ketone, or any radical that can form another lactone.

Preferred examples of odoriferous amines are:
1-methyl-1-(4-methyl-3-cyclohexen-1-yl)ethyl anthranilic acid; benzopyrrole; 8,8-di(1H-indol-3-yl)-2,6-dimethyl-octane-2-ol; anthranilic acid allyl ester; anthranilic acid 1,5-dimethyl-1-vinyl-4-hexenyl ester; 2-amino-benzoic acid methyl ester*; methyl anthranilic acid N-(2-methylpent-1-en-1-yl) ester; anthranilic acid phenylethyl ester*; 2-methylamino-benzoic acid methyl ester*; 6-methyltetrahydroquinoline; isobutyl N-methyl anthranilate; (Z)-3-hexenyl 2-aminobenzoate*, whereby the asterisks indicate the more preferred odoriferous amides.

A wide variety of non-odoriferous amines can also be used for the preparation of the amides according to the invention. For example, a list of suitable primary and secondary cosmetic amines can be found in the 'Cosmetic Ingredient Handbook' edited by Joanne M. Nikitakis. Suitable surfactant amines can be found, for example, in 'Surfactants Europa' edited by Gordon L. Hollis. Amino acids such as glycine, leucine, tyrosine, serine, glutamic acid, aspartic acid, phenylalanine, alanine, lysine, arginine, histidine, cysteine, valine, proline, tryptophan, isoleucine, methionine, asparagine, glutamine and threonine may also be used.

The present invention is described in the following examples which are presented solely for the non-limiting purpose of further illustrating the invention.

EXAMPLE 1

(a) 4-Oxo-decanoic acid 3,7-dimethyl-oct-6-enyl ester

According to Synthesis, 1987, 408, a solution of 20.0 g 4-oxo-1-decanoic acid 16.8 g citronellol extra and, 0.5 g p-toluenesulfonic acid in 150 ml of cyclohexane was refluxed in a flask equipped with a Dean-Stark trap for 3 hours. Then the reaction mixture was cooled, diluted with ether, washed with saturated $NaHCO_3$ and water. The organic phase was dried, filtered and evaporated to dryness. The resulting oil was purified by chromatography to yield 31.7 g of a yellow oil.

NMR ($CDCl_3$) $\delta$5.04–5.19 (m, 1H), 4.11–4.17 (m, 2H), 2.68–2.79 (m, 2H), 2.53–2.60 (m, 2H), 2.41–2.48 (t, 2H), 2.03–1.91 (q, 2H), 1.75–1.44 (m, 6H), 1.43–1.08 (m, 12H), 0.92–0.84 (m, 6H)

(b) According to the same procedure, 5-oxo-dodecanoic acid 3,7-dimethyl-oct-6-enyl ester was prepared from 5-oxo-dodecanoic acid, citronellol and p-toluenesulfonic acid.

(c) According to the same procedure, 4-oxo-decanoic acid hex-3-enyl ester was prepared from 4-oxo-decanoic acid, cis-3-hexenol and p-toluenesulfonic acid.

(d) According to the same procedure, 4-oxo-decanoic acid 2-phenethyl ester was prepared from 4-oxo-decanoic acid, 2-phenyl ethanol and p-toluenesulfonic acid.

(e) According to the same procedure, 4-oxo-nonanoic acid 3,7-dimethyl-oct-6-enyl ester was prepared from 4-oxo-nonanoic acid, citronellol and p-toluenesulfonic acid.

(f) According to the same procedure, 4-oxo-nonanoic acid phenethyl ester was prepared from 4-oxo-nonanoic acid, 2-phenyl ethanol and p-toluenesulfonic acid.

(g) According to the same procedure, 4-oxo-nonanoic acid hex-3-enyl ester was prepared from 4-oxo-nonanoic acid, cis-3-hexenol and p-toluenesulfonic acid.

(h) According to the same procedure, 4-oxo-undecanoic acid phenethyl ester was prepared from 4-oxo-undecanoic acid, 2-phenyl ethanol and p-toluenesulfonic acid.

(i) According to the same procedure, 4-oxo-undecanoic acid hex-3-enyl ester was prepared from 4-oxo-undecanoic acid, cis-3-hexenol and p-toluenesulfonic acid.

(j) According to the same procedure, 4-oxo-undecanoic acid 2-(4-oxo-undecanoyloxy)-ethyl ester was prepared from 4-oxo-undecanoic acid, ethylene glycol and p-toluenesulfonic acid.

EXAMPLE 2

(a) 4-Oxo-decanoic acid 3,7-dimethyl-oct-2,6-dienyl ester

A solution of 5.2 g 4-oxo-decanoic acid, 13.5 g geraniol, 17.5 g N,N'-dicyclohexyl-carbodiimide and 1.0 g 4-pyrrolidinopyridine in 250 ml of dichloromethane was stirred for 24 hours at room temperature. The precipitate was filtered off, the filtrate was diluted with ether, washed with aqueous hydrochloric acid, saturated NaHCO$_3$ and brine. The organic phase was dried, filtered and evaporated to dryness. The resulting oil-cristall mixture was purified by chromatography to yield 19.7 g of a colourless oil.

NMR (CDCl$_3$) δ5.13–5.04 (m, 1H), 4.15–4.02 (q, 2H), 3.60 (s, 1H), 2.49–2.37 (t, 2H), 2.06–1.92 (m, 2H), 1.60 (s, 6H), 1.56–1.17 (m, 12H), 0.93–0.85 (q, 3H)

(b) According to the same procedure, 5-oxo-decanoic acid 3,7-dimethyl-oct-2,6-dienyl ester was prepared from 5-oxo-decanoic acid and geraniol.

(c) According to the same procedure, 4-oxo-nonanoic acid 3,7-dimethyl-octa-2,6-dienyl ester was prepared from 4-oxo-nonanoic acid and geraniol.

(d) According to the same procedure, 4-oxo-decanoic acid 1,1,5-trimethyl-exyl ester was prepared from 4-oxo-decanoic acid and 2,6-dimethyl-heptan-2-ol.

(e) According to the same procedure, 4-oxo-decanoic acid 1,5-dimethyl-1-vinyl-hex-4-enyl ester was prepared from 4-oxo-decanoic acid and (±)-linalool.

(f) According to the same procedure, 4-oxo-decanoic acid 1,1,5-trimethyl-hept-6-enyl ester was prepared from 4-oxo-decanoic acid and 2,6-dimethyl-oct-7-en-2-ol.

(g) According to the same procedure, 4-oxo-undecanoic acid 3,7-dimethyl-octa-2,6-dienyl ester was prepared from 4-oxo-undecanoic acid and geraniol.

(h) According to the same procedure, 4-oxo-undecanoic acid 2-benzyloxycarbonyl-2-benzyloxycarbonylamino-ethyl ester was prepared from 4-oxoundecanoic acid and 2-benzyloxycarbonylamino-3-hydroxy-propionic acid benzyl ester.

EXAMPLE 3

(a) 4-Hydroxy-decanoic acid 3,7-dimethyl-oct-6-enyl ester

A solution of 2,0 g sodium borohydride in 30 ml of water was cooled to 5° C. A solution of 4-oxo-decanoic acid 3,7-dimethyl-oct-6-enyl ester in 75 ml of THF was added to the reaction during 12 minutes and the resulting reaction mixture was stirred at room temperature for 5 hours. Then the reaction mixture was diluted with ether, washed with saturated NaHCO$_3$, brine and water. The organic phase was dried, filtered and evaporated to dryness. The resulting liquid was purified by chromatography to yield 7.6 g of a liquid.

(b) According to the same procedure, 4-hydroxy-decanoic acid 3,7-dimethyl-oct-2,6-dienyl ester was prepared from 4-oxo-decanoic acid 3,7-dimethyl-octa-2,6-dienyl ester, sodium borohydride and water.

(c) According to the same procedure, 5-hydroxy-dodecanoic acid 3,7-dimethyl-oct-6-enyl ester was prepared from 5-oxo dodecanoic acid 3,7-dimethyl-oct-6-enyl ester, sodium borohydride and water.

(d) According to the same procedure, 5-hydroxy-dodecanoic acid 3,7-dimethyl-oct-2,6-dienyl ester was prepared from 5-oxo dodecanoic acid 3,7-dimethyl-oct-2,6-dienyl ester, sodium borohydride and water.

(e) According to the same procedure, 4-hydroxy-decanoic acid hex-3-enyl ester was prepared from 4-oxo-decanoic acid hex-3-enyl ester, sodium borohydride and water.

(f) According to the same procedure, 4-hydroxy-decanoic acid 2-phenethyl ester was prepared from 4-oxo-decanoic acid 2-phenethyl ester, sodium borohydride and water.

(g) According to the same procedure, 4-hydroxy-decanoic acid 1,5-dimethyl-1-vinyl-hex-4-enyl ester was prepared from 4-oxo-decanoic acid 1,5-dimethyl-1-vinyl-hex-4-enyl ester, sodium borohydride and water.

(h) According to the same procedure, 4-hydroxy-decanoic acid 1,1,5-trimethyl-hept-6-enyl ester was prepared from 4-oxo-decanoic acid 1,1,5-trimethyl-hept-6-enyl ester, sodium borohydride and water.

(i) According to the same procedure, 4-hydroxy-decanoic acid 1,1,5-trimethyl-hexyl ester was prepared from 4-oxo-decanoic acid 1,1,5-trimethyl-hexyl ester, sodium borohydride and water.

(j) According to the same procedure, 4-hydroxy-undecanoic acid 3,7-dimethyl-oct-6-enyl ester was prepared from 4-oxo-undecanoic acid 3,7-dimethyl-oct-6-enyl ester, sodium borohydride and water.

(k) According to the same procedure, 4-hydroxy-undecanoic acid phenethyl ester was prepared from 4-oxo-undecanoic acid phenethyl ester, sodium borohydride and water.

(l) According to the same procedure, 4-hydroxy-undecanoic acid hex-3-enyl ester was prepared from 4-oxo-undecanoic acid hex-3-enyl ester, sodium borohydride and water.

(m) According to the same procedure, 4-hydroxy-nonanoic acid 3,7-dimethyl-octa-2,6-dienyl ester was prepared from 4-oxo-nonanoic acid 3,7-dimethyl-octa-2,6-dienyl ester, sodium borohydride and water.

(n) According to the same procedure, 4-hydroxy-nonanoic acid 3,7-dimethyl-oct-6-enyl ester was prepared from 4-oxo-nonanoic acid 3,7-dimethyl-oct-6-enyl ester, sodium borohydride and water.

(o) According to the same procedure, 4-hydroxy-nonanoic acid hex-3-enyl ester was prepared from 4-oxo-nonanoic acid hex-3-enyl ester, sodium borohydride and water.

(p) According to the same procedure, 4-hydroxy-nonanoic acid phenethyl ester was prepared from 4-oxo-nonanoic acid phenethyl ester, sodium borohydride and water.

EXAMPLE 4

(a) 4-Hydroxy-undecanoic acid sodium salt

To a solution of 43.6 g sodium hydroxide in 150 ml of methanol heated to reflux, 200 g gamma-undecalactone were dropped in. After stirring 2 hours at reflux, the mixture was cooled to room temperature and evaporated to dryness. The resulting crystals were washed with hexane to yield 240 g white crystals.

NMR (CDCl$_3$) δ5.1–4.8 (br s, OH), 3.63–3.42 (m, 1H), 2.39–2.20 (t, 2H), 1.89–1.52 (m, 2H), 1.51–1.15 (m, 12H), 1.00–0.81 (t, 3H) ppm.

(b) According to the same procedure, 3-(1-hydroxy-4-isopropyl-cyclohexyl)-propionic acid sodium salt was prepared from 8-(1-methylethyl)-1-oxaspiro[4,5]-decan-2-one and sodium hydroxide.

EXAMPLE 5

1-Chloro-3,7-dimethyl-octa-2,6-diene

To a mixture of 170 g linalool and 20 mg bismuth(III)-oxide heated to 60° C., 130.5 g trimethylchlorosilane were dropped in. Then the mixture was cooled to room temperature and the organic layer was separated. The resulting oil was purified by distillation to yield 158.35 g of a colorless oil.

NMR (CDCl$_3$) δ5.56–5.35 (t, 1H), 5.18–4.99 (m, 1H), 4.16–4.02 (d, 2H), 2.26–1.91 (m, 4H), 1.89–1.45 (m, 9H) ppm.

EXAMPLE 6

(a) 4-Hydroxy-undecanoic acid 3,7-dimethyl-octa-2,6-dienyl ester

A mixture of 155 g 1-chloro-3,7-dimethyl-octa-2,6-diene, 202 g 4-hydroxy-undecanoic acid sodium salt and 5 g tetrabutylammoniumbromide in 800 ml of dimethylformamide was heated to 50° C. After stirring for 24 hours, the mixture was cooled to room temperature and filtered through Celite. The filtrate was diluted with ether, washed with water, 2N HCl, saturated sodium bicarbonate and brine. The organic phase was dried and evaporated to dryness. The resulting yellow oil was purified by wipe film distillation to yield 96.6 g of a yellow oil.

NMR (CDCl$_3$) δ5.42–5.37 (t, 1H), 5.16–5.01 (m, 1H), 4.65–4.53 (m, 2H), 3.69–3.52 (m, 1H), 2.60–2.22 (m, 2H), 2.20–1.95 (m, 4H), 1.89–1.12 (m, 24H), 1.02–0.78 (t, 3H) ppm.

(b) According to the same procedure, 3-(1-hydroxy-4-isopropyl-cyclohexyl)-propionic acid 3,7-dimethyl-octa-2,6-dienyl ester was prepared from 1-chloro-3,7-dimethyl-octa-2,6-diene, 3-(1-hydroxy-4-isopropyl-cyclohexyl)-propionic acid sodium salt and tetrabutylammoniumbromide.

EXAMPLE 7

(a) 4-Hydroxy-undecanoic acid 2-(4-hydroxy-undecanoyloxy)-ethyl ester

To a solution of 21.54 g 4-oxo-undecanoic acid 2-(4-oxo-undecanoyloxy)-ethyl ester and a of bromocresol green in 150 ml of methanol, 6.34 g sodium cyanoborohydride was added. The resulting reaction mixture was stirred for 2.5 hours at room temperature, while dropping in 2N HCl to adjust the pH<3.8. The solvent was then evaporated, the solid residue was dissolved in ether and washed with water. The organic phase was dried and evaporated to dryness to yield the compound.

NMR (CDCl$_3$) δ4.35–4.20 (m, 4H), 3.87–3.53 (m, 2H), 2.54–2.39 (t, 4H), 2.05–1.13 (m, 28H), 1.04–0.80 (t, 6H) ppm.

(b) According to the same procedure, 4-hydroxy-undecanoic acid 2-benzyloxycarbonyl-2-benzyloxycarbonylamino-ethyl ester was prepared from 4-oxo-undecanoic acid 2-benzyloxycarbonyl-2-benzyloxycarbonylamino-ethyl ester, sodium cyanoborohydride and methanol.

EXAMPLE 8

Test cloth was washed with a lipase-containing detergent to which one or more delayed release fragrances had been added. Headspace analysis of the wet and dry laundry indicated the presence of the fragrant alcohols and lactones. The alcohol and lactone level was higher than when the test cloth was washed with a lipase-containing detergent to which one or more fragrant alcohols and lactones were added. The compounds in Examples 3, 6, 7, 12, 13 and 15 were tested in this way.

EXAMPLE 9

Test cloth was washed with a lipase-containing detergent and then a fabric softener, containing one or more delayed release fragrances, was added to the rinse cycle. Headspace analysis of the wet and dry laundry indicated the presence of the fragrant alcohols and lactones. The alcohol and lactone level was higher than when the test cloth was washed with a lipase-containing detergent and then a fabric softener, containing one or more fragrant alcohols and lactones, was added to the rinse cycle. The compounds in Examples 3, 6, 7, 12, 13 and 15 were tested in this way.

EXAMPLE 10

Axilla bacteria cultures containing 0.1% precursor I were incubated for 20 hours at 30° C. After filtration from the cells, the presence of the parent alcohol and lactone was in each case detected by headspace-GC techniques and/or the majority of an 18 member panel.

The same tests were carried out with inactivated cultures (85°/20 min). The odour of the parent alcohols and lactones could not be detected after incubation, excluding therefore a hydrolysis by the medium or the culture. The compounds in Examples 3, 6, 7, 12, 13 and 15 were tested in this way.

EXAMPLE 11

The following set forth examples for the use of the delayed release fragrances of the present invention in various products. The compounds in Examples 3, 6, 7, 12, 13, and 15 were tested in this way. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones and the like. All products can also be buffered to the desired pH. All values are % w/w.

| Deo-colognes | I | II | III | IV |
|---|---|---|---|---|
| Delayed Release Fragrances | 0.5 | 1.5 | 2.5 | 6.0 |
| Fragrance | 0.5 | 1.5 | 2.5 | 6.0 |
| Triclosan (Ciba Geigy) | 1.0 | — | 0.75 | 1.0 |
| Alcohol to | 100.0 | 100 | 100 | 100 |

Deo-Sticks

| Antiperspirant | |
|---|---|
| Ethylene Glycol Monostearate | 7.0 |
| Shea butter | 3.0 |
| Neobee 1053 (PVO International) | 12.0 |
| Generol 122 (Henkel) | 5.0 |
| Kesscowax B (Akzo) | 17.0 |
| Dimethicone Dow Corning 345 | 35.0 |
| Aluminum Sesquichlorhydrate | 20.0 |
| Delayed Release Fragrances | 0.5 |
| Fragrance | 0.5 |
| Antiperspirant | |
| Steary Alcohol | 17.0 |
| Castor Wax | 3.0 |
| Talc | 5.0 |
| Aluminum Zirconium Tetrachlorhydrate | 20.0 |
| Delayed Release Fragrances | 1.0 |
| Fragrance | 1.0 |
| Dimethicone Dow 245 | to100.0 |
| Clear Deodorant Stick | |
| Witconol APM | 43.0 |
| Propylene Glycol | 20.0 |
| Alcohol 39C | 20.0 |
| Demin water | 7.0 |
| Monamid 150ADD | 5.0 |
| Millithix 925 | 2.0 |
| Ottasept Extra | 0.5 |
| Delayed Release Fragrances | 0.75 |
| Fragrance | 0.75 |
| Deodorant Stick | |
| Propylene Glycol | 69.0 |
| Demin Water | 21.8 |
| Triclosan | 0.2 |
| Sodium Stearate | 8.0 |
| Delayed Release Fragrances | 0.5 |
| Fragrance | 0.5 |

-continued

| Alcohol free Deodorant Stick | |
|---|---|
| PPG-3 Myristyl Ether (Witconol APM) | 36.0 |
| Propylene Glycol | 36.0 |
| Demin Water | 19.0 |
| Triclosan | 0.25 |
| Sodium Stearate | 7.75 |
| Delayed Release Fragrances | 0.5 |
| Fragrance | 0.5 |
| Antiperspirant Aerosol | |
| Absolute Ethanol | 15.0 |
| Zirconium Aluminum tetrachlorhydrate | 5.0 |
| Bentone 38 | 1.5 |
| Delayed Release Fragrances | 0.75 |
| Fragrance | 0.75 |
| S-31 Hydocarbon propellant | to 100.0 |
| Antiperspirant Pump | |
| Demin water | 57.5 |
| Aluminum Sesquichlorhydrate | 20.0 |
| Triton X-102 (Union Carbide) | 2.0 |
| Dimethyl Isosorbide (ICI) | 20.0 |
| Delayed Release Fragrances | 0.25 |
| Fragrance | 0.25 |
| Roll-On | |
| Dimethicone DC 354 (Dow Corning) | 69.0 |
| Bentone 38 | 10.0 |
| Rezal 36 GP (Reheis Chem. Co.) | 20.0 |
| Delayed Release Fragrances | 0.5 |
| Fragrance | 0.5 |

In the above, the following components were used:

| | |
|---|---|
| Triclosan- | 5-chloro-2-(2,4-dichlorophenoxy)phenol |
| Neobee 1053 | glycerol tricaprate/caprylate |
| Generol 122 | soya sterol |
| Kesscowax B | cetyl alcohol and glycol polymer |
| Witconol APM | polypropylene glycol-3 myristyl ether |
| Monamid 150 ADD | cocoamide diethanolamine |
| Millithix 925 | dibenzylidene sorbitol |
| Ottasept Extra | quaternium 18 hectorite |
| Bentone 38 | quaternium 18 hectorite |
| Triton X-102 | octoxynol-13 |
| Dimethicone DC 354 | mixture of fully methylated linear siloxanepolymers end-blocked with trimethylsiloxy units |
| Rezal 36 GP | Aluminium zirconium tetrachlorohydrexglycine |

EXAMPLE 12

4-Hydroxy-undecanoic acid dodecylamide

To a suspension of 19.0 g aluminum trichloride in 50 ml of dichloromethane, a solution of 46.5 g dodecylamine in 50 ml of dichloromethane was dropped in at 15–20° C. Then 19.3 g gamma-undecalactone were added quickly at room temperature and an additional 50 ml of dichloromethane was added. After 4 hours, the reaction mixture was quenched with water and filtered through celite. The filtrate was diluted with ether and washed with brine. The organic phase was dried, filtered and evaporated to dryness. The resulting brown solid was purified by recrystallisation to yield 2.65 g of colourless crystals.

NMR (CDCl$_3$) δ5.79–5.61 (m, 1H), 3.70–3.54 (m, 1H), 3.31–3.15 (m, 2H), 2.42–2.28 (t, 2H), 1.96–1.10 (m, 34H), 0.97–0.78 (t, 6H).

EXAMPLE 13

(a) 5-Hydroxy-decanoic acid dodecylamide

A mixture of 9.34 g dodecylamine and 8.53 g d-decalactone was heated to 50° C. After 10 minutes, the reaction mixture was cooled to room temperature. The resulting solid was purified by recrystallisation to yield 16.70 g of colourless crystals.

NMR (CDCl$_3$) δ5.70–5.51 (m, 1H), 3.68–3.50 (m, 1H), 3.32–3.16 (m, 2H), 2.30–2.15 (t, 2H), 2.04–1.10 (m, 32H), 1.00–0.80 (t, 6H).

(b) According to the same procedure, 4-hydroxy-pentanoic acid phenethyl-amide was prepared from 6-methyl-pyran-2-one and phenethylamine.

(c) According to the same procedure, 4-hydroxy-undecanoic acid [12-(4-hydroxy-undecanoylamino)-dodecyl]-amide was prepared from 5-heptyldihydro-2(3H)-furanone and 1,12-diaminododecane.

EXAMPLE 14

4-Oxo-pentanoic acid {4-[4-(4-oxo-pentanoylamino)-benzenesulfonyl]-phenyl}-amide This compound was prepared by coupling N-{4-[4-(3-carbonxy-propionylamino)-benzenesulfonyl]-phenyl}-succinamic acid (J. Amer. Chem. Soc., 1945, 67, 1979) with N,O-dimethyl-hydroxyamine followed by reaction with methylmagnesium iodide to yield the solid product.

EXAMPLE 15

4-Hydroxy-pentanoic acid {4-[4-(4-hydroxy-pentanoylamino)-benzenesulfonyl]-phenyl}-amide A solution of sodium borohydride in methanol was cooled to 5° C. A solution of 4-oxo-pentanoic acid {4-[4-(4-oxo-pentanoylamino)-benzenesulfonyl]-phenyl}-amide in THF was added and the resulting reaction mixture was stirred at room temperature. After workup and purification, the product was obtained as a colourless solid.

EXAMPLE 16 a) Fabric softener of the ester quat type (4×concentrate):

| INGREDIENTS | CHEMICAL NAME | % |
|---|---|---|
| PHASE A | | |
| DEIONISED WATER | | to 100.0 |
| MgCl$_2$ (saturated sol.) | Magnesium chloride | 1.0 |
| PHASE B | | |
| REWOQUAT WE 18 | Di-(tallow carboxyethyl)hydroxy ethyl methylammonium methosulfate | 15.0 |
| GENAPOL O 100 | Ethoxylated fatty alcohol C16–C18 10EO | 2.0 |
| ANTIFOAM DB 31 | | 0.5 |
| PHASE C | | |
| ISOPROPYL ALCOHOL | | 3.0 |
| PRESERVATIVE | | Qs |
| PERFUME | | Qs |

Process

While stirring and heating to 65° C. phase A was mixed with phase B which has been preheated to 65° C. After cooling to room temperature phase C was added.

The PH value of the finished product is 2.60. It turned out that the recommended level of perfume is 1.0%. Delayed release fragrances then could be any part of this 1.0%.

b) Fabric softener of the ester quat type (1×concentrate):

| INGREDIENTS | CHEMICAL NAME | % |
|---|---|---|
| PHASE A | | |
| DEIONISED WATER | | to100.0 |
| PHASE B | | |
| REWOQUAT WE 18 | Di-(tallowcarboxyethyl)-hydroxy ethyl methylammonium methosulfate | 6.0 |
| DOBANOL 25-9 | Ethoxylated fatty alcohol C12–C15 9EO | 0.50 |
| ANTIFOAM DB 31 | | 0.10 |
| PHASE C | | |
| MYACIDE BT 30 | 2-bromo-2-nitropropane 1,3 diol | 0.03 |
| PROXEL GXL | Benzisothiazolinone sodium salt | 0.02 |
| PERFUME | | Qs |

Process

While stirring and heating to 65° C. phase A was mixed with phase B which has been preheated to 65° C. After cooling to room temperature, phase C was added.

The pH value of the finished product was 3.5. It turned out that the recommended level of perfume is 0.3%. Delayed release fragrances then could be any part of this 0.3%.

What is claimed is:

1. A precursor compound having the formula

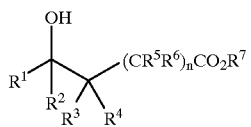

Ia in which n is 1, 2 or 3 and $R^1$ to $R^6$ represent, independently, substituted or unsubstituted alkyl-, alkenyl-, alkinyl-, cycloalkyl-, cycloalkenyl- or aromatic-radicals or hydrogen wherein these radicals may in addition contain one or more —O— and/or

groups, $R^7$ represents a radical of a fragrant alcohol $R^7OH$ having 6 or more carbon atoms wherein one or two rings can be built by the combination of the respective $R^1$ to $R^6$ and this/these ring(s) can be further substituted by an alkyl-group.

2. A precursor compound having the formula

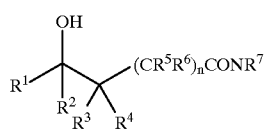

Ib in which n is 1, 2 or 3 and $R^1$ to $R^6$ represent, independently, branched or unbranched, substituted or unsubstituted alkyl-, alkinyl-, cycloalkyl-, cycloalkenyl- or aromatic-radicals or hydrogen wherein these radicals may in addition contain one or more —O— and/or

groups, wherein one or two rings can be built by the combination of the respective $R^1$ to $R^6$ and this/these ring(s) can be further substituted by an alkyl-group, and $R^7$ represents a radical of an amine $R^{7'}R^{7''}NH$, wherein $R^{7'}$ and $R^{7''}$ represent, independently, branched or unbranched, substituted or unsubstituted alkyl-, alkenyl-, alkinyl-, cycloalkyl-, cycloalkenyl- or aromatic radicals or either $R^{7'}$ or $R^{7''}$ may be hydrogen, wherein the amine is a fragrant amine or the amine has more than 9 C atoms, wherein $R^{7'}$ and/or $R^{7''}$ may further contain at least one remaining part $C(OH)R^1R^2$—$CR^3R^4$—$(CR^5R^6)_n$—CO— of formula Ib.

3. A compound according to claims 1 or 2, wherein n is 1 or 2.

4. A compound according to claims 1 or 2, wherein $R^1$ is an alkyl-radical and $R^2$ to $R^6$ are hydrogen atoms.

5. A compound according to claims 1 or 2, wherein $R^1$, $R^3$ are alkyl-radicals and $R^2$, $R^4$, $R^5$, and $R^6$ are hydrogen atoms.

6. A compound according to claims 1 or 2, wherein $R^1$ and $R^2$ build a ring.

7. A compound according to claim 6, wherein the ring is a 6-membered ring.

8. A compound according to claim 7, wherein the ring is substituted by methyl-, ethyl- or isopropyl-.

9. A compound according to claim 1, wherein $R^7$ is a radical derived from a fragrant alcohol or a fragrant phenol.

10. A compound according to claims 1 or 9, wherein the fragrant alcohol or fragrant phenol is selected from the group consisting of hexyl alcohol, 2-hexyl alcohol, heptyl alcohol, octyl alcohol, nonyl alcohol, decyl alcohol, undecyl alcohol, lauryl alcohol, myristic alcohol, 3-methyl-but-2-en-1-ol, 3-methyl-1-pentanol, cis-3-hexenol, cis-4-hexenol, 3,5,5-trimethyl hexanol, 3,4,5,6,6-pentamethylheptan-2-ol, citronellol, geraniol, oct-1-en-3-ol, 2,5,7-trimethyl octan-3-ol, 2-cis-3,7-dimethyl-2,6-octadien-1-ol, 6-ethyl-3-methyl-5-octen-1-ol, 3,7-dimethyl-oct-3,6-dienol, 3,7-dimethyloctanol, 7-methoxy-3,7-dimethyl-octan-2-ol, cis-6-nonenol, 5-ethyl-2-nonanol, 6,8-dimethyl-2-nonanol, 2,2,8-trimethyl-7 (8)-nonene-3-ol, nona-2,6-dien-1-ol, 4-methyl-3-decen-5-ol, dec-9-en-1-ol, benzylalcohol, 2-methyl undecanol, 10-undecen-1-ol, 1-phenyl ethanol, 2-phenyl ethanol, 2-methyl-3-phenyl-3-propenol, 2-phenyl propanol, 3-phenyl propanol, 4-phenyl-2-butanol, 2-methyl-5-phenyl pentanol, 2-methyl-4-phenyl-pentanol, 3-methyl-5-phenyl-pentanol, 2-(2-methylphenyl)-ethanol, 4-(1-methylethyl) benzene methanol, 4-(4-hydroxyphenyl)butan-2-one, 2-phenoxy ethanol, 4-(1-methylethyl)-2-hydroxy-1-methyl benzene, 2-methoxy-4-methyl phenol, 4-methyl phenol, anisic alcohol, p-tolyl alcohol, cinnamic alcohol, vanillin, ethyl vanillin, eugenol, isoeugenol, thymol, anethol, decahydro 2-naphthalenol, borneol, cedrenol, farnesol, fenchyl alcohol, menthol, 3,7,11-trimethyl-2,6,10-dodecatrien-1-ol, alpha ionol, tetrahydro ionol, 2-(1,1-dimethylethyl)cyclohexanol, 3-(1,1 dimethylethyl)cyclohexanol, 4-(1,1 dimethylethyl) cyclohexanol, 4-isopropyl cyclohexanol, 6,6-dimethyl-bicyclo[3,3,1]hept-2-ene-2-ethanol, 6,6-dimethyl-bicyclo[3,1,1]hept-2-ene-methanol, p-menth-8-en-3-ol, 3,3,5-trimethyl cyclohexanol, 2,4,6-trimethyl-3-cyclohexenyl-methanol, 4-(1-methylethyl)cyclohexyl-methanol, 4-(1,1-dimethylethyl)cyclohexanol, 2-(1,1-dimethylethyl)-cyclohexanol, 2,2,6-trimethyl-alpha-propyl cyclohexane propanol, 5-(2,2,3-trimethyl-3-cyclopentenyl)-3-methylpentan-2-ol, 3-methyl-5-(2,2,3-trimethylcyclopentyl-3-enyl)pent-4-en-2-ol, 2-ethyl-4(2,2,3-trimethylcyclopentyl-3-enyl)but-2-en-1-ol, 4-(5,5,6-trimethylbicyclo[2,2.1]hept-2-yl)-cyclohexanol, 2-(2-methylpropyl)-4-hydroxy-4-methyl-tetrahydropyran, 2-cyclohexyl propanol, 2-(1,1-dimethylethyl)-4-methyl cyclohexanol, 1-(2-tert-butyl-cyclohexyloxy)-2-butanol, 1-(4-isopropyl-cyclohexyl)-ethanol, and linalool.

11. A compound according to claims 9 or 10, wherein the radical is derived from a fragrant alcohol or phenol selected from the group consisting of hexyl alcohol, 2-hexyl alcohol, heptyl alcohol, octyl alcohol, nonyl alcohol, decyl alcohol, undecyl alcohol, lauryl alcohol, 3-methyl-but-2-en-1-ol, cis-3-hexenol, cis-4-hexenol, 3,4,5,6,6-pentamethylheptan-2-ol, citronellol, geraniol, 6-ethyl-3-methyl-5-octen-1-ol, 3,7-dimethyl-oct-3,6-dienol, 3,7-dimethyloctanol, 7-methoxy-3,7-dimethyl-octan-2-ol, cis-6-nonenol, 6,8-dimethyl-2-nonanol, 4-methyl-3-decen-5-ol, 1-phenyl ethanol, 2-phenyl ethanol, 2-phenyl propanol, 3-phenyl propanol, 2-methyl-5-phenyl pentanol, 2-methyl-4-phenyl-pentanol, 3-methyl-5-phenyl-pentanol, 2-(2-methylphenyl)-ethanol, 4-(4-hydroxyphenyl)butan-2-one, 2-phenoxy ethanol, anisic alcohol, p-tolyl alcohol, cinnamic alcohol, vanillin, ethyl vanillin, eugenol, isoeugenol, anethol, borneol, cedrenol, farnesol, fenchyl alcohol, menthol, alpha ionol, tetrahydro ionol, 2-(1,1-dimethylethyl)cyclohexanol, 3-(1,1-dimethylethyl)cyclohexanol, 4-(1,1-dimethylethyl)cyclohexanol, 6,6-dimethyl-bicyclo [3,1,1]hept-2-ene-methanol, p-menth-8-en-3-ol, 2,4,6-trimethyl-3-cyclohexenyl-methanol, 4-(1-methylethyl)cyclohexyl-methanol, 2,2,6-trimethyl-alpha-propyl cyclohexane propanol, 5-(2,2,3-trimethyl-3-cyclopentenyl)-3-methylpentan-2-ol, 3-methyl-5-(2,2,3-trimethylcyclopentyl-3-enyl)pent-4-en-2-ol, 2-ethyl-4-(2,2,3-trimethylcyclopentyl-3-enyl)but-2-en-1-ol, 4-(5,5,6-trimethylbicyclo[2,2,1]hept-2-cyclohexanol, 2-(2-methylpropyl)-4-hydroxy-4-methyl-tetrahydropyran, 2-cyclohexyl propanol, 2-(1,1-dimethylethyl)-4-methyl cyclohexanol, 1-(2-tert-butyl-cyclohexyloxy)-2-butanol, 1-(4-isopropyl-cyclohexyl)-ethanol, 2,6-dimethyl-heptan-2-ol, and 2,6-dimethyl-oct-7-en-2-ol.

12. A compound according to claim 11 wherein the radical is derived from a fragrant alcohol or phenol selected from the group consisting of citronellol, geraniol, linalool, cis-3-hexenol, 4-methyl-3-decen-5-ol, 2-phenyl ethanol, iso eugenol, 3-methyl-5-(2,2,3-trimethylcyclopentyl-3-enyl)pent-4-en-2-ol, 2-ethyl-4-(2,2,3-trimethylcyclopentyl-3-enyl)but-2-en-2-ol, 2,6-dimethyl-heptan-2-ol, 2,6-dimethyl-oct-7-en-ol, cinnamic alcohol, and eugenol.

13. A compound according to claim 12 wherein the radical is derived from a fragrant alcohol selected from the group consisting of citronellol, 2-phenyl ethanol, linalool, geraniol, and cis-3-hexanol.

14. A compound according to claims 1 or 2, which upon cleavage, provides lactones with organoleptic properties wherein the lactones are selected from a group consisting of 6-methyl-pyran-2-one, 5-heptyldihydro-2(3H)-furanone, 5-pentyldihydro-2(3H)-furanone, 5-(3-hexenyl)dihydro-5-methyl-(Z)-2(3H)-furanone, 5-hexyldihydro-5-methyl-2(3H)-furanone, 5-hexyldihydro-2(3H)-furanone, 5-octyldihydro-2(3H)-furanone, 8-(1-methylethyl)-1-oxaspiro[4,5]-decan-2-one, 8-methyl-1-oxaspiro[4,5]-decan-2-one, 8-ethyl-1-oxaspiro[4,5]-decan-2-one, 5-(1,5-dimethyl-4-hexenyl)dihydro-2(3H)-furanone, 2-oxo-5-butyl-tetrahydrofuran, 4-methyl-5-pentyl-dihydro-2(3H)-furan-2-one, 5-hexyldihydro-5-methyl-2(3H)-furanone, dihydro-5-methyl-5-vinyl-2(3H)-furanone, octahydro-2H-1-benzopyran-2-one, tetrahydro-6-pentyl-2H-pyran-2-one, tetrahydro-6-hexyl-2H-pyran-2-one, tetrahydro-6-heptyl-2H-pyran-2-one, tetrahydro-6-(3-pentenyl)-(E)-2H-pyran-2-one and tetrahydro-6-(2-pentenyl)-(Z)-2H-pyran-2-one.

15. A compound according to claim 14, wherein the lactones are selected from the group consisting of 5-heptyldihydro-2(3H)-furanone, 5-pentyldihydro-2(3H)-furanone, 5-hexyldihydro-2(3H)-furanone, 8-(1-methylethyl)-1-oxaspiro[4,5]-decan-2-one and 2-oxo-5-butyl-tetrahydrofuran.

16. A compound according to claim 1 wherein the compound is selected from the group consisting of 4-hydroxy-decanoic acid 2-phenethyl ester, 4-hydroxy-decanoic acid 3,7-dimethyl-oct-6-enyl ester, 4-hydroxy-decanoic acid hex-3-enyl ester, 4-hydroxy-decanoic acid 3,7-dimethyl-oct-2,6-dienyl ester, 5-hydroxy-dodecanoic acid 3,7-dimethyl-oct-6-enyl ester, 5-hydroxy-dodecanoic acid 3,7-dimethyl-oct-2,6-dienyl ester, 4-hydroxy-undecanoic acid 3,7-dimethyl-oct-6-enyl ester, 4-hydroxy-undecanoic acid 3,7-dimethyl-oct-2,6-dienyl ester, 4-hydroxy-decanoic acid 1,5-dimethyl-1-vinyl-hex-4-enyl ester, 4-hydroxy-decanoic acid 1,1,5-trimethyl-hept-6-enyl ester, 4-hydroxy-decanoic acid 1,1,5-trimethyl-hexyl ester, 4-hydroxy-undecanoic acid 3,7-dimethyl-oct-6-enyl ester, 4-hydroxy-undecanoic acid phenethyl ester, 4-hydroxy-undecanoic acid hex-3-enyl ester, 4-hydroxy-nonanoic acid 3,7-dimethyl-octa-2,6-dienyl ester, 4-hydroxy-nonanoic acid 3,7-dimethyl-oct-6-enyl ester, 4-hydroxy-nonanoic acid hex-3-enyl ester, 4-hydroxy-nonanoic acid phenethyl ester, 3-(1-hydroxy-4-isopropyl-cyclohexyl)-propionic acid 3,7-dimethyl-octa-2,6-dienyl ester, 4-hydroxy-undecanoic acid 2-(4-hydroxy-undecanoyloxy)-ethyl ester, and 4-hydroxy-undecanoic acid 2-benzyloxycarbonyl-2-benzyloxcarbonylamino-ethyl ester.

17. A compound according to claim 2 wherein $R^7$ is a radical from an odoriferous amine.

18. A compound according to claim 17 wherein the odoriferous amine is selected from the group consisting of 1-methyl-1-(4-methyl-3-cyclohexen-1-yl)ethyl anthranilic acid, benzopyrrole, 8,8-di(1H-indol-3-yl)-2,6-dimethyl-octane-2-ol, anthranilic acid allyl ester, anthranilic acid 1,5-dimethyl-1-vinyl-4-hexenyl ester, 2-amino-benzoic acid methyl ester, methyl anthranilic acid N-(2-methylpent-1-en-1-yl)ester, anthranilic acid phenylethyl ester, 2-methylamino-benzoic acid methyl ester, 6-methyltetrahydro-quinoline, isobutyl N-methyl anthranilate, and (Z)-3-hexenyl 2-aminobenzoate.

19. A compound according to claim 18 wherein the odoriferous amine is selected from the group consisting of 2-amino benzoic acid methyl ester, anthranilic acid phenyl-ethyl ester, 2-methylamino-benzoic acid methyl ester, and (Z)-3-hexenyl 2-aminobenzoate.

20. A compound according to claim 2 selected from the group consisting of 4-hydroxy-undecanoic acid dodecylamide, 5-hydroxy-decanoic acid dodecylamide, 4-oxo-pentanoic acid{4-[4-(4-oxo-pentanoylamino)-benzenesulfonyl]-phenyl}-amide-4-hydroxy-pentanoic acid{4-[4-(4-hydroxy-pentanoylamino)-benzenesulfonyl]-phenyl}-amide, and 4-hydroxy-undecanoic acid[12-(4-hydroxy-undecanoylamino)-dodecyl]-amide.

21. A compound according to claims 1 or 2, wherein the compound is cleavable by heat.

22. A composition for cosmetic application to the human skin, air fresheners, hard surface cleaners or laundry products, which composition comprises at least one of the compounds according to claims 1 or 2.

23. A process for prolonging the effect of diffusion of the characteristic odor of an odoriferous compound selected from the group consisting of an odoriferous alcohol, an odoriferous amine, an odoriferous lactone, and mixtures thereof comprising applying a compound according to claim 1 or 2 to a substrate selected from the group consisting of human skin, an air freshener, a hard surface cleaner, and a laundry product.

24. A method of suppressing human body malodor comprising applying a composition according to claim 22 to the human skin.

25. A process for imparting a fragrance and/or an antibacterial effect to a substrate comprising:
(a) exposing a composition comprising a compound according to claims 1 or 2 to a substrate selected from the group consisting of human hair, human skin, air, a hard surface, and laundry; and
(b) allowing the compound to be cleaved to provide the fragrance and/or antibacterial effect to the substrate.

26. A compound having the formula

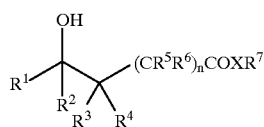
I in which n is 1, 2 or 3 and $R^1$ to $R^6$ represent, independently, branched or unbranched, substituted or unsubstituted alkyl-, alkenyl-, alkinyl-, cycloalkyl-, cycloalkenyl- or aromatic-radicals or hydrogen wherein these radicals may in addition contain one or more —O— and/or

groups, wherein one or two rings can be built by the combination of the respective $R^1$ to $R^6$ and this/these ring(s) can be further substituted by an alkyl-group, in which X is either O and $R^7$ represents a radical of a fragrant alcohol having 6 or more carbon atoms or phenol $R^7OH$ or X is N and $R^7$ represents a radical of an amine $R^{7'}R^{7''}NH$, wherein $R^{7'}$ and $R^{7''}$ represent, independently, branched or unbranched, substituted or unsubstituted alkyl-, alkenyl-, alkinyl-, cycloalkyl-, cycloalkenyl- or aromatic radicals or either $R^{7'}$ or $R^{7''}$ may be hydrogen, wherein the amine is a fragrant amine or the amine has more than 9 C atoms, wherein $R^7$ of the alcohol or phenol and $R^{7'}$ and/or $R^{7''}$ of the amine, respectively, may further contain at least one remaining part $C(OH)R^1R^2$—$CR^3R^4$—$(CR^5R^6)_n$—CO— of formula I.

27. A compound selected from the group consisting of 4-hydroxy-decanoic acid-2-phenethyl ester, 4-hydroxy-decanoic acid 3,7-dimethyl-oct-6-enyl ester, 4-hydroxy-decanoic acid hex-3-enyl ester, 4-hydroxy-decanoic acid 3,7-dimethyl-oct-2,6-dienyl ester, 5-hydroxy-dodecanoic acid 3,7-dimethyl-oct-6- enyl ester, 5-hydroxy-dodecanoic acid 3,7-dimethyl-oct-2,6-dienyl ester, 4-hydroxy-undecanoic acid 3,7-dimethyl-oct-6-enyl ester, 4-hydroxy-undecanoic acid 3,7-dimethyl-oct-2,6-dienyl ester, 4-hydroxy-decanoic acid 1,5-dimethyl-1-vinyl-hex-4-enyl ester, 4-hydroxy-decanoic acid 1,1,5-trimethyl-hept-6-enyl ester, 4-hydroxy-decanoic acid 1,1,5-trimethyl-hexyl ester, 4-hydroxy-undecanoic acid 3,7-dimethyl-oct-6-enyl ester, 4-hydroxy-undecanoic acid phenethyl ester, 4-hydroxy-undecanoic acid hex-3-enyl ester, 4-hydroxy-nonanoic acid 3,7-dimethyl-octa-2,6-dienyl ester, 4-hydroxy-nonanoic acid 3,7-dimethyl-oct-6-enyl ester, 4-hydroxy-nonanoic acid hex-3-enyl ester, 4-hydroxy-nonanoic acid phenethyl ester, 3-(1-hydroxy-4-isopropyl-cyclohexyl)-propionic acid 3,7-dimethyl-octa-2,6-dienyl ester, and 4-hydroxy-undecanoic acid 2-(4-hydroxy-undecanoyloxy)-ethyl ester.

28. A compound selected from the group consisting of 4-hydroxy-undecanoic acid dodecylamide, 5-hydroxy-decanoic acid dodecylamide, 4-hydroxy-pentanoic acid{4-[4-(4-hydroxy-pentanoylamino)-benzenesulfonyl]-phenyl}-amide, and 4-hydroxy-undecanoic acid[12-(4-hydroxy-undecanoylamino)-dodecyl]-amide.

29. A process according to claim 25, wherein the composition is selected from the group consisting of a cosmetic, an air freshener, a hard surface cleaner, and a laundry product.

30. A process according to claim 23 further comprising applying an additional compound according to claims 1 or 2 to the substrate.

* * * * *